(12) United States Patent
Okai et al.

(10) Patent No.: US 11,821,865 B2
(45) Date of Patent: Nov. 21, 2023

(54) GAS SENSOR

(71) Applicant: NGK SPARK PLUG CO., LTD., Nagoya (JP)

(72) Inventors: Masana Okai, Nagoya (JP); Takehiro Oba, Nagoya (JP); Daisuke Tahira, Nagoya (JP); Masashi Nomura, Nagoya (JP)

(73) Assignee: NITERRA CO., LTD., Nagoya (JP)

( * ) Notice: Subject to any disclaimer, the term of this patent is extended or adjusted under 35 U.S.C. 154(b) by 78 days.

(21) Appl. No.: 17/046,224

(22) PCT Filed: Feb. 8, 2019

(86) PCT No.: PCT/JP2019/004622
§ 371 (c)(1),
(2) Date: Oct. 8, 2020

(87) PCT Pub. No.: WO2019/244391
PCT Pub. Date: Dec. 26, 2019

(65) Prior Publication Data
US 2021/0072177 A1    Mar. 11, 2021

(30) Foreign Application Priority Data

Jun. 19, 2018   (JP) ................................. 2018-115924

(51) Int. Cl.
*G01N 27/28*     (2006.01)
*G01N 27/407*    (2006.01)
*G01N 33/00*     (2006.01)

(52) U.S. Cl.
CPC ......... *G01N 27/283* (2013.01); *G01N 27/407* (2013.01); *G01N 33/0036* (2013.01)

(58) Field of Classification Search
CPC ............... G01N 27/283; G01N 27/407; G01N 27/4077; G01N 27/4078
See application file for complete search history.

(56) References Cited

FOREIGN PATENT DOCUMENTS

| DE | 102017003445 A1 * | 10/2017 | ......... G01N 27/4078 |
| JP | 2004-198363 | 7/2004 | |
| JP | 4815257 B2 * | 11/2011 | |

(Continued)

OTHER PUBLICATIONS

International Search Report for PCT/JP2019/004622 dated Apr. 16, 2019 [PCT/ISA/210].

*Primary Examiner* — Caitlyn Mingyun Sun
(74) *Attorney, Agent, or Firm* — Sughrue Mion, PLLC (57) ABSTRACT

A gas sensor including: a sensor element extending in an axial direction; a metal shell surrounding and supporting the sensor element; an exterior tube that is tubular and is mounted to a rear end of the metal shell; a metal terminal including a first end connected to a lead wire and a second end electrically connected to the sensor element; a separator that is tubular and is disposed in the exterior tube and contains the metal terminal and the sensor element; and a holder being in contact with the separator in the axial direction. The holder includes ribs formed in a frontward face or a rearward face of the holder and arranged at predetermined intervals in a circumferential direction. Each of the ribs occupies a region having a length equal to or greater than a thickness of the holder, as viewed in the axial direction.

6 Claims, 6 Drawing Sheets

(56) References Cited

FOREIGN PATENT DOCUMENTS

| JP | 2012-225737 | A |   | 11/2012 |
|----|-------------|---|---|---------|
| JP | 2015-132493 | A |   | 7/2015  |
| JP | 2015132493  | A | * | 7/2015  |
| JP | 2016099268  | A | * | 5/2016  |
| JP | 2016211981  | A | * | 12/2016 |

* cited by examiner

GAS SENSOR

CROSS REFERENCE TO RELATED APPLICATIONS

This application is a National Stage of International Application No. PCT/JP2019/004622 filed Feb. 8, 2019, claiming priority based on Japanese Patent Application No. 2018-115924 filed Jun. 19, 2018.

TECHNICAL FIELD

The present invention relates to art for a gas sensor.

BACKGROUND ART

Patent Document 1 discloses an example of a gas sensor structured to be mounted to an exhaust passage of an internal combustion engine such as an automobile engine, wherein the gas sensor includes a detector element structured to produce output variable depending on a concentration of specific gas, such as NOx (nitrogen oxide) and oxygen, in exhaust gas. The detector element includes at least one cell including a pair of electrodes disposed in a solid electrolyte, and is structured to measure the concentration of specific gas, based on signal outputted from the cell depending on the concentration of specific gas.

The detector element is contained in a metal shell for mounting the gas sensor to the exhaust pipe. The detector element includes a rear end formed to project rearward with respect to the metal shell and be surrounded by an exterior tube mounted to a rear end of the metal shell. The detector element includes at its rear end, electrode pads for extraction of the output. The electrode pads are electrically connected to an external circuit via lead wires and metal terminals. The exterior tube further surrounds a separator made of insulator ceramic. The separator contains the metal terminals so as to maintain them noncontact with each other.

The separator and the exterior tube interpose therebetween a holder containing and holding the separator. The holder includes: a tubular portion surrounding an outer periphery of the separator; supporter portions disposed rearward with respect to the tubular portion and arranged at intervals in a circumferential direction; and inner extension portions each of which is disposed between the supporter portions. The supporter portions are in contact with the separator to support the separator in an axial direction. In detail, the supporter portions restrict a frontward move of the separator in the axial direction. The inner extension portions are in contact with the outer periphery of the separator so as to support the separator pinchingly in a radial direction.

PRIOR ART DOCUMENT(S)

Patent Document(s)

Patent Document 1: JP 2012-225737 A

SUMMARY OF THE INVENTION

Problem(s) to be Solved by the Invention

However, each of the supporter portions of the conventional holder has a structure flexible enough to allow a force for holding the separator to be released. Accordingly, the conventional holder is incomplete in the restriction of axial move of the separator in case that the separator receives vibration from the outside. This allows the separator to wobble, and may cause the metal terminals to undergo fatigue fracture due to repeated contact between the metal terminals inside the separator and an inner periphery of the separator. This may deteriorate the detector element and the metal terminals in reliability of electrical connection therebetween.

Means for Solving the Problem(s)

In view of the foregoing, it is desirable to solve the above problem. The following mode or embodiment of the present invention serves for that.

According to a first aspect of the present invention, a gas sensor includes: a sensor element for sensing a concentration of a specific gas, wherein the sensor element extends in an axial direction; a metal shell surrounding and supporting the sensor element; an exterior tube that is tubular and is mounted to a rear end of the metal shell; a metal terminal including a first end connected to a lead wire and a second end electrically connected to the sensor element; a separator that is tubular and is disposed in the exterior tube and contains the metal terminal and the sensor element; and a holder being in contact with the separator in the axial direction, wherein: the holder includes a plurality of ribs formed in a frontward face or a rearward face of the holder and arranged at predetermined intervals in a circumferential direction; and each of the plurality of ribs occupies a region having a length equal to or greater than a thickness of the holder, as viewed in the axial direction.

According to the first aspect of the gas sensor, the ribs are formed in the frontward face or the rearward face of the holder and are arranged at the predetermined intervals in the circumferential direction. This serves to enhance rigidity in the axial direction of a vicinity of a contact region between the holder and the separator. This serves to reduce flexibility of the holder and suppress the separator from wobbling.

In the first aspect of the gas sensor, each of the plurality of ribs includes an unevenness with a difference in elevation. The gas sensor according to this aspect serves to enhance rigidity of the ribs, and is desirable in that point.

In the first aspect of the gas sensor, the holder may include a tubular portion, an outer bent portion, and supporter portions, wherein: the tubular portion surrounds an outer periphery of the separator; the outer bent portion is connected to a rear end of the tubular portion over a circumference thereof, and is bent inwardly in the radial direction to decrease in diameter; the supporter portions are connected to an inner end in the radial direction of the outer bent portion, and are arranged at intervals in the circumferential direction, and extend inwardly in the radial direction so as to support the separator in the axial direction; and each of the plurality of ribs is formed in a corresponding one of the supporter portions.

The gas sensor according to this aspect serves to enhance rigidity of the supporter portions of the holder which contact and support the separator, and is desirable in that point.

In the first aspect of the gas sensor, the holder may further include a plurality of inner extension portions connected to the inner end in the radial direction of the outer bent portion, wherein: each of the plurality of inner extension portions is disposed between a pair of the supporter portions adjacent to each other, and includes an inner bent portion bent to a front end side in the axial direction, and includes a front-end-side end being in contact with the outer periphery of the separator; and the plurality of inner extension portions support the separator pinchingly in the radial direction due to the contact between the front-end-side ends of the plurality of inner extension portions and the outer periphery of the separator.

The gas sensor according to this aspect serves to suppress the separator from wobbling, by supporting the separator pinchingly in the radial direction, and is desirable in that point.

MODE(S) FOR CARRYING OUT THE INVENTION

Figure 1:
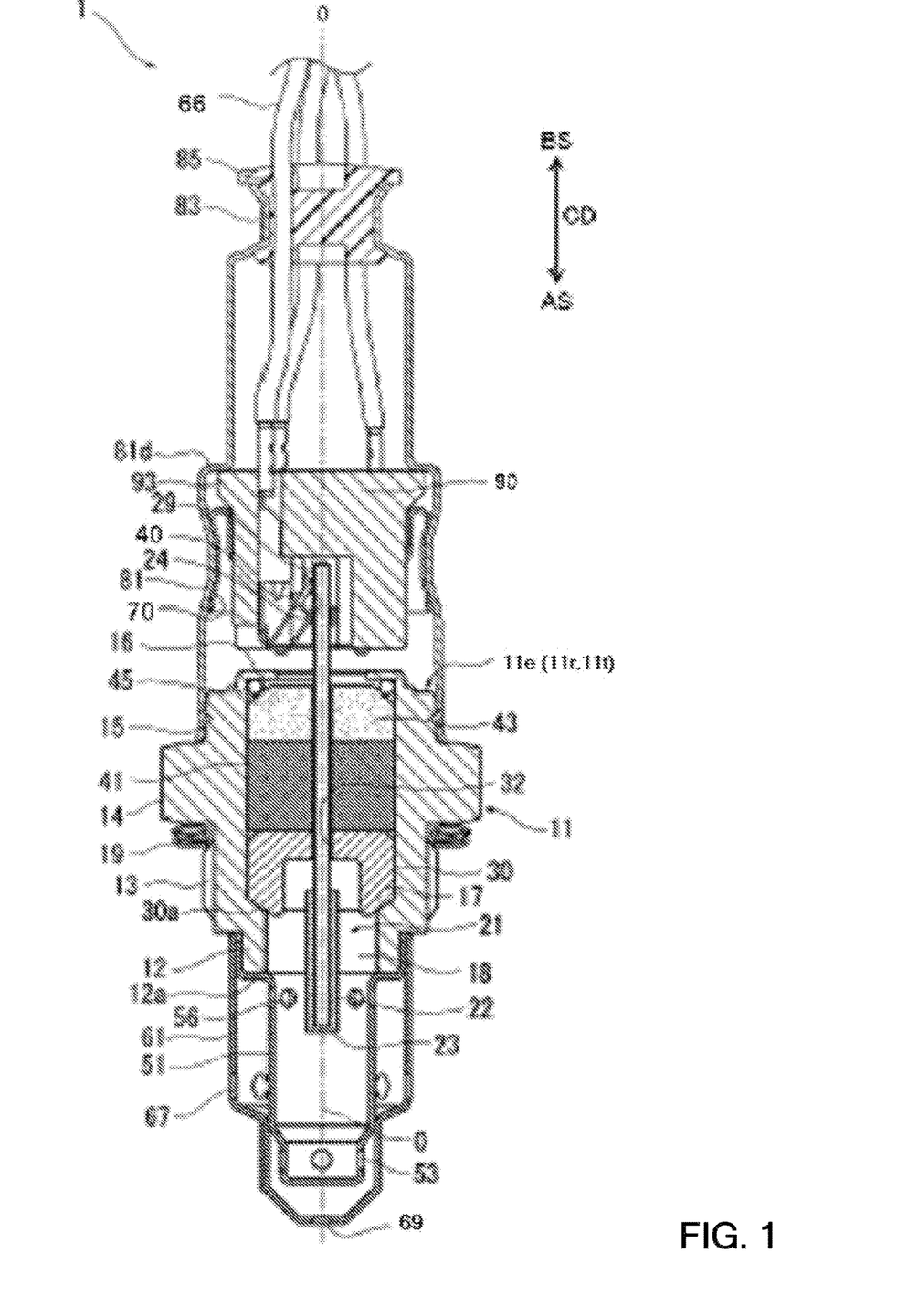
FIG. 1 is a longitudinal sectional view of a gas sensor according to a first embodiment of the present invention.

The following describes an embodiment of the present invention. FIG. 1 is a longitudinal sectional view of a gas sensor 1 according to the first embodiment of the present invention. FIG. 1 presents as a vertical direction, an axial direction CD parallel with an axis O (shown as a dash-dot line) of the gas sensor 1. Furthermore, a lower end side of a sensor element 21 in FIG. 1 is referred to as a front end side AS of the gas sensor 1, and an upper end side of the sensor element 21 in FIG. 1 is referred to as a rear end side BS of the gas sensor 1.

As shown in FIG. 1, the gas sensor 1, which is a whole region air-fuel ratio gas sensor, includes the sensor element 21, a ceramic holder 30, and a metal shell 11. The ceramic holder 30 includes a through hole 32 extending in a direction of the axis O for insertion of the sensor element 21. The metal shell 11 is disposed to circumferentially surround an outer periphery of the ceramic holder 30. The sensor element 21 includes a detector 22 in its front-end-side section projecting frontward with respect to the ceramic holder 30. The sensor element 21 is thus-inserted in the through hole 32 and fixed in its longitudinal direction inside the metal shell 11, with airtightness maintained by compressing a seal material 41, which is a talc in the present embodiment, in the longitudinal direction via a sleeve 43 and a ring washer 45 that are made of insulator. Furthermore, the sensor element 21 includes a rear end 29 and electrode terminals 24 in its rear-end-29-side section projecting rearward with respect to the sleeve 43 and the metal shell 11. The electrode terminals 24 are in pressure contact with metal terminals 40 of lead wires 66 for electrical connection, wherein the lead wires 66 are extracted to the outside through a seal material 85. The rear-end-29-side section including the electrode terminals 24 is covered by an exterior tube 81. The following provides detailed description.

The sensor element 21 has a shape of belt-like board extending in the direction of axis O, and includes the detector 22 in the front-end-side section (i.e. a lower-end-side section in the drawing) to be directed toward an measuring object. The detector 22 includes detector electrodes not shown, and is structured to detect a specific gas component in target gas. The sensor element 21 is shaped long and narrow with a rectangular cross section constant in size in the longitudinal direction, and is mainly made of ceramic such as solid electrolyte. The sensor element 21 itself is similar to conventionally known one, in which: a pair of detector electrodes composing the detector 22 is formed in a front-end-side section of a solid electrolyte member; and in connection with this, the electrode terminals 24 are exposedly formed in a rear-end-side section of the solid electrolyte member, for extraction of detection output via the lead wires 66. Furthermore, according to the present embodiment, the sensor element 21 includes: a heater (not shown) formed inside a front-end-side section of a ceramic member stacked with the solid electrolyte member; and the electrode terminals 24 exposedly formed in the rear-end-side section of the solid electrolyte member in order to be connected to the lead wires 66 for voltage application on the heater. Although not shown, each of the electrode terminals 24 has a rectangular shape vertically long, and, in the rear-end-29-side section of the sensor element 21, exemplarily two or three of the electrode terminals 24 are horizontally arranged on each of both wide faces of the belt-like board shape. In addition, the detector 22 of the sensor element 21 is covered by a protective layer 23 formed porous and made of alumina, spinel, etc.

The metal shell 11 is shaped tubular and has concentric various diameters in the longitudinal direction. The metal shell 11 includes: an annular portion (or a cylindrical portion) 12 that has a cylindrical shape with a front end smaller in diameter, and is structured such that protectors 51 and 61 are externally fitted and fixed to the annular portion 12; a screw portion 13 that is disposed in an outer periphery of a section rearward (i.e. upper in the drawing) of the annular portion 12, and is greater in diameter than the annular portion 12, and is used for mounting to an exhaust pipe of an engine; a polygonal portion 14 that is disposed rearward with respect to the screw portion 13, and is used for screwing-in of the gas sensor 1 using the screw portion 13; a cylindrical portion 15 that is disposed rearward with respect to the polygonal portion 14, and is structured such that the exterior tube 81 as a protector tube is externally fitted and welded to the cylindrical portion 15 so as to cover a rear section of the gas sensor 1; and a calking cylindrical portion 16 that is disposed rearward with respect to the cylindrical portion 15, and is smaller in diameter and thinner than the cylindrical portion 15. The calking cylindrical portion 16 in FIG. 1 is one after calking, and is drawn as bent inwardly. The polygonal portion 14 is drawn with a gasket 19 mounted to a lower end thereof for sealing upon the screwing-in. Furthermore, the metal shell 11 includes an inner hole 18 extending through the metal shell 11 in the direction of axis O. The inner hole 18 includes an inner periphery including a step portion 17 shaped to radially inwardly taper in a direction from the rear end side toward the front end side.

The metal shell 11 contains the ceramic holder 30 made of insulator ceramic such as alumina and shaped as a short cylinder substantially. The ceramic holder 30 includes a frontward face 30a shaped to radially inwardly taper in the direction toward the front end side. The frontward face 30a includes an outer periphery to be engaged with the step portion 17. Furthermore, the ceramic holder 30 is pressed from the rear end side by the seal material 41. This determines a position of the ceramic holder 30 in loose fit in the metal shell 11. At a center of the ceramic holder 30, the through hole 32 is formed as a rectangular opening having a substantially same size with the cross section of the sensor element 21 such that the sensor element 21 is inserted in the through hole 32 with substantially no gap.

The sensor element 21 extends through the through hole 32, and includes a front end projecting frontward with respect to the ceramic holder 30 and a front end 12*a* of the metal shell 11. According to the present embodiment, the front-end-side section of the sensor element 21 has two-layer structure, and is covered by the protectors (i.e. protection covers) 51 and 61 that respectively include air vents 56 and 67. Each of the protectors 51 and 61 is shaped as a cylinder with a bottom. The protector 51, which is an inner one of these two, includes a rear end externally fitted and welded to the cylindrical portion 12 of the metal shell 11. The air vents 56 are formed in a rear end of the protector 51, at exemplarily eight points in a circumferential direction. The protector 51 further includes in its front end, outlets 53 formed at exemplarily four points in the circumferential direction. The protector 61, which is an outer one of the two protectors, is externally fitted to the inner protector 51, and is simultaneously welded to the cylindrical portion 12 of the metal shell 11. The air vents 67 of the protector 61 are formed in a front-end-side section thereof, at exemplarily eight points in the circumferential direction. The protector 61 further includes an outlet 69 at a center of a bottom of a front end thereof.

The electrode terminals 24 in the rear-end-29-side section of the sensor element 21 are in pressure contact with the metal terminals 40 due to elasticity of the metal terminals 40, so as to establish electrical connection therebetween, wherein the metal terminals 40 are formed at tips of the lead wires 66 leading to the outside through the seal material 85. The metal terminals 40 including these pressure contact parts are respectively contained oppositely to each other in containers formed in the separator 90 that is disposed in the exterior tube 81 and serves as an insulator. The separator 90 is restricted in radial move and in move toward the front end, by a holder 70 fixed by calking in the exterior tube 81. The exterior tube 81 includes a front end externally fitted and welded to the cylindrical portion 15 formed in a rear-end-side section of the metal shell 11, and thereby the rear section of the gas sensor 1 is airtightly covered. The lead wires 66 are extracted to the outside through the seal material 85, such as rubber, disposed inside a rear end of the exterior tube 81, where airtightness is established by calking a small-diameter tubular portion 83 in order to reduce its diameter.

In addition, the exterior tube 81 includes a step portion 81*d* in a section slightly rearward with respect to a center of the exterior tube 81 in the direction of axis O. The step portion 81*d* is shaped to increase in diameter toward its front end, and includes an inner periphery formed to press forward a rear end of the separator 90 so as to support it. The separator 90 includes in its outer periphery a flange 93 supported on the holder 70 fixed inside the exterior tube 81. Thus, the separator 90 is held in the direction of axis O by the step portion 81*d* and the holder 70.

Figure 2:
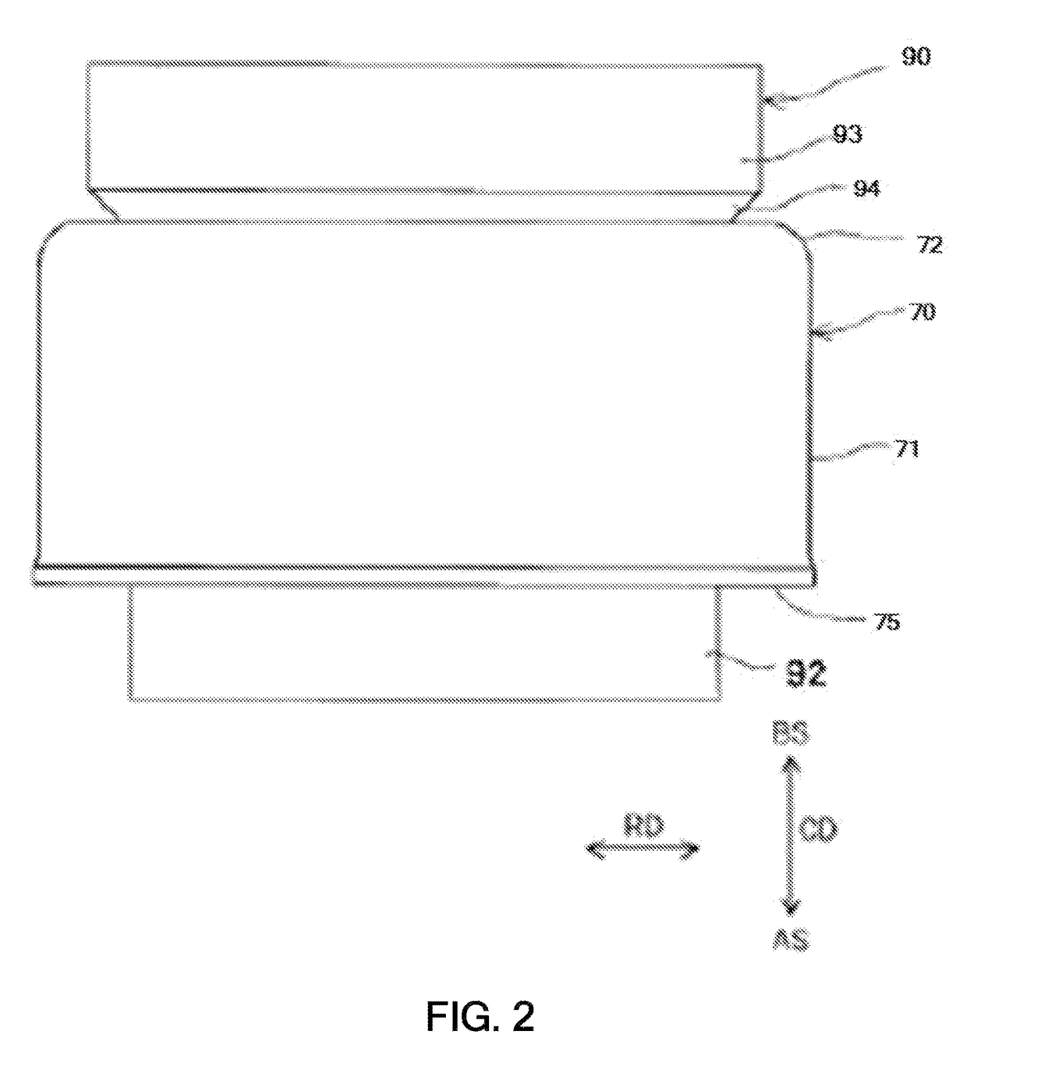
FIG. 2 is an illustrative view of a holder holding a separator.
Figure 3:
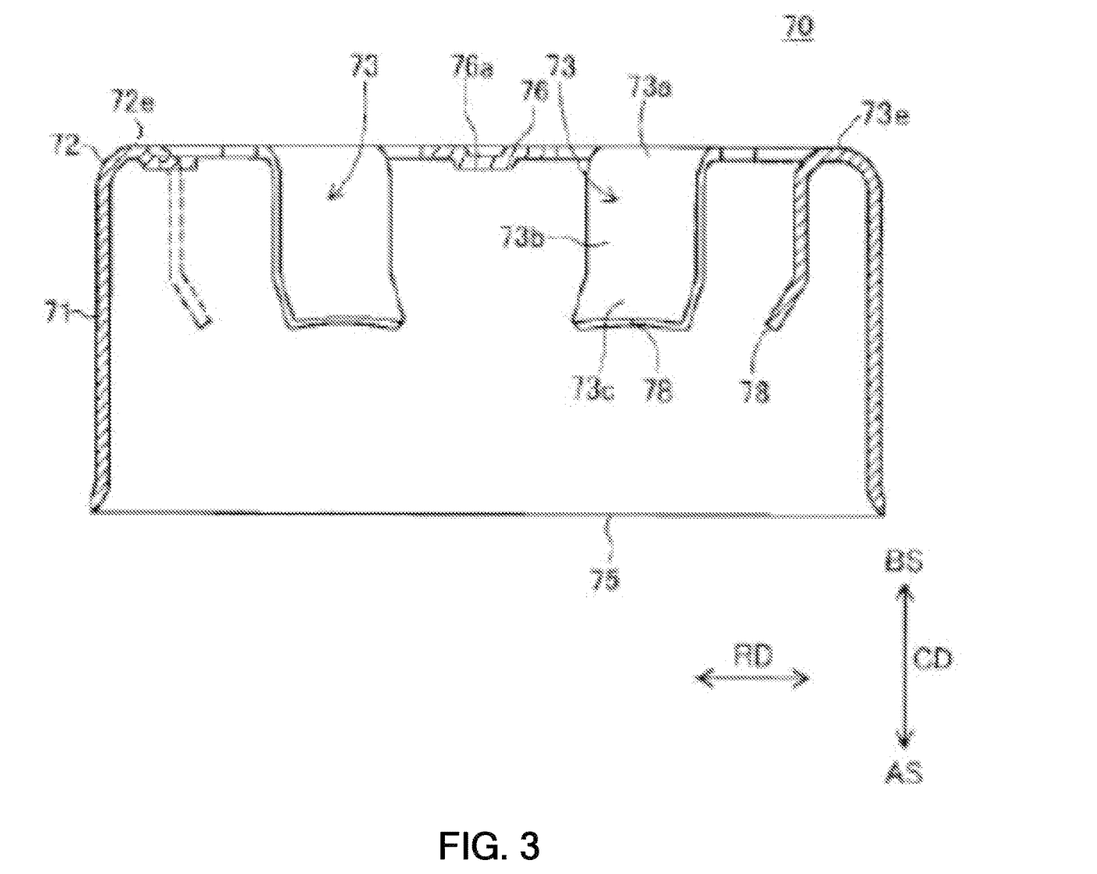
FIG. 3 is a longitudinal sectional view of the holder.
Figure 4:
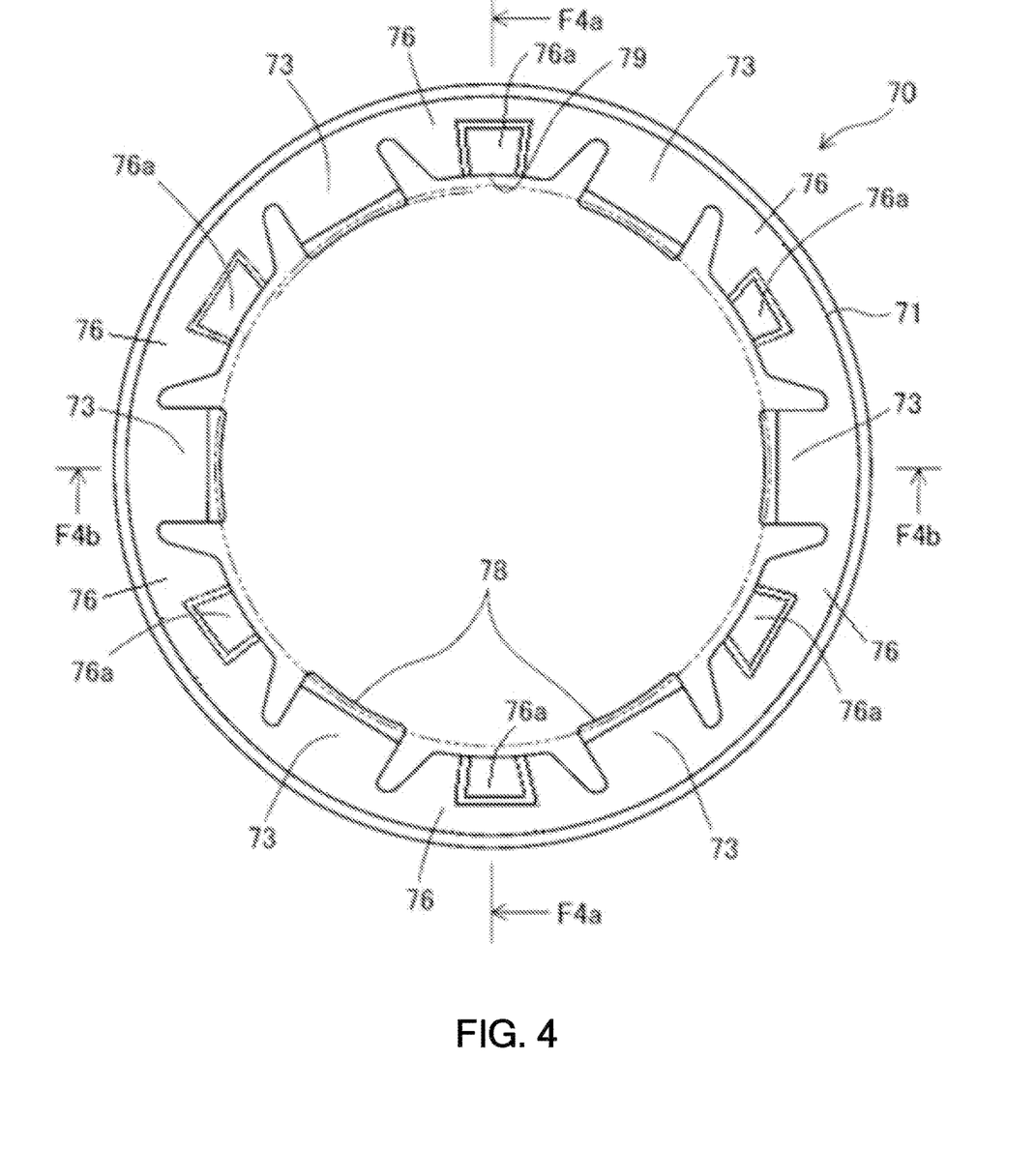
FIG. 4 is a top view of the holder.
Figure 5:
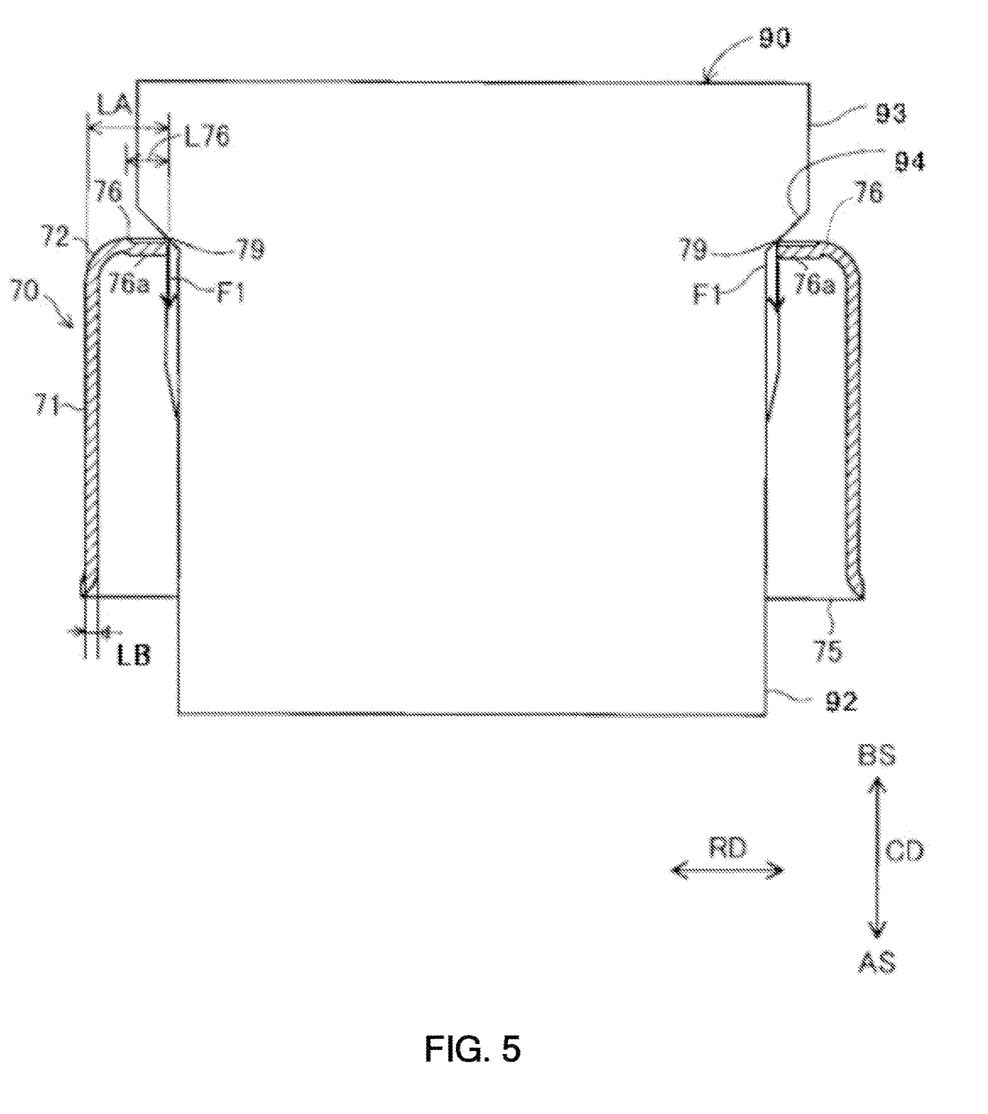
FIG. 5 is a longitudinal sectional view of the holder along a line F4a-F4a shown in FIG. 4.
Figure 6:
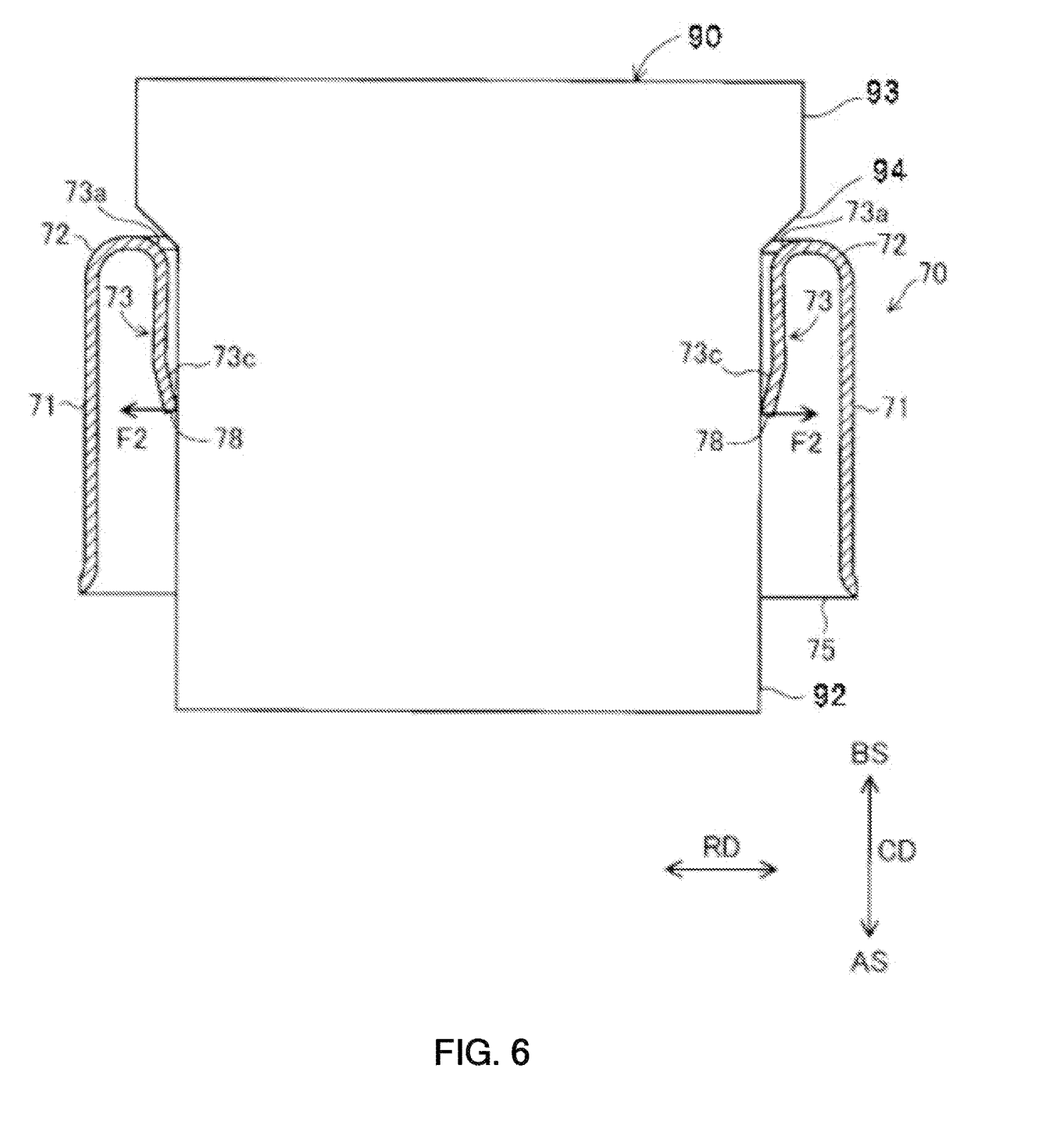
FIG. 6 is a longitudinal sectional view of the holder along a line F4b-F4b shown in FIG. 4.

FIG. 2 shows the holder 70 supporting the separator 90. FIG. 3 is a sectional view of the holder 70. FIG. 4 is a top view of the holder 70. FIG. 5 is a sectional view along a line F4*a*-F4*a* shown in FIG. 4. FIG. 6 is a sectional view along a line F4*b*-F4*b* shown in FIG. 4. Each of FIGS. 2, 3, 5, and 6 shows a tubular portion 71 before deformed due to the calking of the exterior tube 81. Each of FIGS. 2, 3, 5, and 6 shows as an arrow representing a radial direction RD of the holder 70. FIG. 4 includes a dash two-dot line showing a position to which an outer periphery 92 of the separator 90 is to be laid upon mounting the holder 70 to the gas sensor 1. Each of FIGS. 5 and 6 shows the separator 90 without its detailed internal structure.

As shown in FIG. 2, the separator 90 is inserted in the holder 70 shaped tubular. The separator 90 includes the rear end projecting to the rear end side BS with respect to the holder 70, and includes a front end projecting to the front end side AS from a front end opening 75 of the holder 70.

As shown in FIGS. 3 and 4, the holder 70 includes the tubular portion 71, an outer bent portion 72, supporter portions 76, and inner extension portions 73. The tubular portion 71 is disposed to surround the outer periphery 92 of the separator 90, as shown in FIG. 2. As shown in FIG. 3, the outer bent portion 72 is connected to a rear end of the tubular portion 71, and is shaped to be bent inwardly in the radial direction RD to decrease in diameter. In detail, the outer bent portion 72 is bent to be convex upward such that a center of an arc thereof is positioned in the front end side AS. The outer bent portion 72 is connected to the rear end of the tubular portion 71 over a circumference thereof.

As shown in FIG. 3, each of the supporter portions 76 extends inwardly in the radial direction RD from an end 72*e* that is an inner end in the radial direction RD of the outer bent portion 72. According to the first embodiment, each of the supporter portions 76 extends in a direction parallel with the radial direction RD. As shown in FIG. 4, the supporter portions 76 are arranged at intervals in the circumferential direction, at six points according to the present embodiment. Each of the supporter portions 76 includes a rib 76*a* extending outwardly in the radial direction RD from an end 79. Thus, a plurality of the ribs 76*a* are arranged at intervals in the circumferential direction, at six points according to the present embodiment. Each of the ribs 76*a* includes an unevenness with a difference in elevation in the axial direction. As shown in FIG. 5, the ends 79, which are inner ends of the supporter portions 76 in the radial direction RD, support the separator 90 in the axial direction CD by contacting with the tapering portion 94. Specifically, the ends 79 are in contact with the tapering portion 94, and thereby restrict move of the separator 90 in a direction to the front end side AS. Here, a force F1 represents a force exerted on each of the ends 79 from the separator 90 in the direction to the front end side AS. A maximum length LA represents a maximum in length in the radial direction RD from the tubular portion 71 to the end 79 being a position of contact between the supporter portion 76 and the separator 90. A length L76 represents a length in the radial direction RD of a region occupied by the rib 76*a* of the supporter portion 76. According to the present embodiment, the maximum length LA is equal to a length from the end 79 of the supporter portion 76 to the outer periphery of the tubular portion 71 before the deformation, because, as shown in FIG. 1, the tubular portion 71 includes the deformation due to calking, not in a section around the rear end of the tubular portion 71 but in only a central section of the tubular portion 71.

As shown in FIG. 4, according to the present embodiment, the length L76 of the region occupied by the rib 76*a* of the supporter portion 76 in the radial direction RD is greater than a thickness of the holder. Specifically, the region of the rib 76*a* of the supporter portion 76 has a length greater than a length LB between the outer periphery and the inner periphery of the tubular portion 71 of the holder. The supporter portions 76 have rigidity enhanced by forming the ribs 76*a* occupying the regions having such lengths in the supporter portions 76. This serves to enhance the restriction of the move of the separator 90 in the direction to the front end side AS, and suppress the separator 90 from wobbling.

As shown in FIG. 4, each of the inner extension portions 73 is disposed between a pair of the supporter portions 76 adjacent to each other in the circumferential direction.

According to the present embodiment, the inner extension portions 73 are disposed at six points. As shown in FIG. 3, each of the inner extension portions 73 includes an inner bent portion 73a, an inner straight portion 73b, and an inner contact portion 73c. Each of the inner bent portions 73a is connected to a corresponding one of the end 72e, and is formed to be bent to the front end side AS. In detail, each of the inner bent portions 73a is bent to be convex upward such that a center of an arc thereof is positioned in the front end side AS. The inner straight portion 73b has a shape of flat plate, and extends to the front end side AS from an inner end in the radial direction RD of the inner bent portion 73a. The inner contact portion 73c extends inwardly in the radial direction RD, from an end of the front end side AS of the inner straight portion 73b. The inner straight portion 73b and the inner contact portion 73c are formed to be elastically deformable in the radial direction RD. As shown in FIG. 6, each of front-end-side ends 78 having an arc shape is in contact with the outer periphery 92 all over the arc. In a state that the outer periphery 92 is inserted in the tubular portion 71, each of the inner extension portions 73 (i.e. the inner contact portion 73c) receives a force F2 from the outer periphery 92 in the radial direction RD, and thereby elastically deforms outwardly in the radial direction RD with respect to a free state. Thus, the inner contact portions 73c hold the separator 90 as nipping it internally in the radial direction RD. This partially determines a position in the radial direction RD of the separator 90.

The present invention is not limited to the above embodiment or configurations, and may be carried out in various modes without departing from scope of the invention. Although the above embodiment exemplifies a gas sensor structured to detect oxygen in exhaust gas flowing in an exhaust pipe of a vehicle, the present embodiment is not limited to such appliance, and may be applied to various gas sensors structured to detect specific gas (e.g. NOx) in other gas.

According to the present embodiment, the length L76, which is the length of the region of the rib 76a in the radial direction RD, is equal to approximately 50% of the maximum length LA that is the length between the tubular portion 71 and the end 79 in the radial direction RD. However, the length L76 may be greater than that, and may have a same value with the maximum length LA. The present invention enhances beneficial effects when within a range of LC≤L76≤LA.

Although the present embodiment exemplifies the rib 76a as the unevenness with the difference in elevation, the supporter portion 76 may include a frontward face or a rearward face that has a depression or a projection, without being limited to such embodiment.

Although the present embodiment exemplifies the rib 76a formed such that an uniform depression and a corresponding projection occupy an entire of the region of the rib 76a, the supporter portion 76 may include a rib formed such that a region of the rib includes a plurality of depressions or projections less in length than LB, without being limited to the above embodiment. For example, such configuration may be achieved by knurling or embossing.

The invention claimed is:

1. A gas sensor comprising:
a sensor element for sensing a concentration of a specific gas, wherein the sensor element extends in an axial direction;
a metal shell surrounding and supporting the sensor element;
an exterior tube that is tubular and is mounted to a rear end of the metal shell;
a metal terminal including a first end connected to a lead wire and a second end electrically connected to the sensor element;
a separator that is tubular and is disposed in the exterior tube and contains the metal terminal and the sensor element; and
a holder being in contact with the separator in the axial direction,
wherein:
the holder includes a tubular portion and a plurality of ribs;
the tubular portion surrounds an outer periphery of the separator;
the plurality of ribs are formed in a frontward face or a rearward face of the holder and arranged at predetermined intervals in a circumferential direction;
each of the plurality of ribs occupies a region having a length L76 in the radial direction that is within a range of from 50% of a maximum length LA up to the maximum length LA, wherein the maximum length LA is equal to a length from an end of the rib to an outer periphery of the tubular portion;
the frontward face of the holder is closer to the sensor element in the axial direction than the rearward face of the holder; and
either the following (A) or (B) is satisfied:
(A) when the plurality of ribs are formed in the frontward face of the holder, each of the plurality of ribs includes at an end portion thereof in the radial direction a depression extending from the frontward face of the holder toward the rearward face of the holder and extending in the radial direction over the entire length L76; or
(B) when the plurality of ribs are formed in the rearward face of the holder, each of the plurality of ribs includes at an end portion thereof in the radial direction a depression extending from the rearward face of the holder toward the frontward face of the holder and extending in the radial direction over the entire length L76.

2. The gas sensor as claimed in claim 1, wherein each of the plurality of ribs includes an unevenness with a difference in elevation.

3. The gas sensor as claimed in claim 1, wherein:
the holder further includes an outer bent portion, and supporter portions;
the outer bent portion is connected to a rear end of the tubular portion over a circumference thereof, and is bent inwardly in the radial direction such that the holder decreases in diameter in the radial direction;
the supporter portions are connected to an inner end in the radial direction of the outer bent portion, and are arranged at intervals in the circumferential direction, and extend inwardly in the radial direction so as to support the separator in the axial direction; and
each of the plurality of ribs is formed in a corresponding one of the supporter portions.

4. The gas sensor as claimed in claim 3, wherein:
the holder further includes a plurality of inner extension portions connected to the inner end in the radial direction of the outer bent portion;
each of the plurality of inner extension portions is disposed between a pair of the supporter portions adjacent to each other, and includes an inner bent portion bent to a front end side in the axial direction, and includes a front-end-side end being in contact with the outer periphery of the separator; and the plurality of inner extension portions support the separator pinchingly in the radial direction due to the contact between the front-end-side ends of the plurality of inner extension portions and the outer periphery of the separator.

5. The gas sensor as claimed in claim 1, wherein:
the plurality of ribs are formed in the frontward face of the holder.

6. The gas sensor as claimed in claim 1, wherein:
the plurality of ribs are formed in the rearward face of the holder.

\* \* \* \* \*